United States Patent [19]
Bourrain et al.

[11] Patent Number: 6,054,469
[45] Date of Patent: Apr. 25, 2000

[54] SUBSTITUTED TETRAHYDROPYRIDINE DERIVATIVES ACTING ON 5-HT RECEPTORS

[75] Inventors: Sylvie Bourrain, Harlow; Angus Murray MacLeod, Bishops Stortford; Graham Andrew Showell, Bury St. Edmunds, all of United Kingdom

[73] Assignee: Merck Sharp & Dohme Ltd., Hoddesdon, United Kingdom

[21] Appl. No.: 09/068,049

[22] PCT Filed: Nov. 13, 1996

[86] PCT No.: PCT/GB96/02763

§ 371 Date: Apr. 29, 1998

§ 102(e) Date: Apr. 29, 1998

[87] PCT Pub. No.: WO97/18204

PCT Pub. Date: May 22, 1997

[30] Foreign Application Priority Data

Nov. 16, 1995 [GB] United Kingdom .................... 9523462

[51] Int. Cl.[7] ....................... A61K 31/4439; A61P 25/06; C07D 401/14
[52] U.S. Cl. ......................................... 514/340; 546/272.4
[58] Field of Search ........................... 546/272.4; 514/340

[56] References Cited

U.S. PATENT DOCUMENTS 5,273,977  12/1993  Glass et al. .

FOREIGN PATENT DOCUMENTS

| 0 470 039 A2 | 2/1992 | European Pat. Off. . |
| 0 545 095 A1 | 6/1993 | European Pat. Off. . |
| 0 683 166 A1 | 11/1995 | European Pat. Off. . |
| 94/02460 | 3/1994 | WIPO . |
| 94/21626 | 9/1994 | WIPO . |
| 94/21627 | 9/1994 | WIPO . |
| 95/29911 | 11/1995 | WIPO . |
| 95/32196 | 11/1995 | WIPO . |

OTHER PUBLICATIONS

Cram and Hammond, "Organic Chemistry", McGraw Hill Book Co., NY, (1964) 2nd ed., pp 565–67.

*Primary Examiner*—Patricia L. Morris
*Attorney, Agent, or Firm*—David L. Rose; James L. McGinnis; Philippe L. Durette

[57] ABSTRACT

Compounds having formula I, or salts or prodrugs thereof:

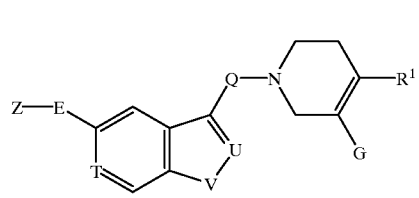

are selective agonists of the 5-$HT_{1D\alpha}$ receptor and are useful in the treatment of migraine and associated conditions.

8 Claims, No Drawings

SUBSTITUTED TETRAHYDROPYRIDINE DERIVATIVES ACTING ON 5-HT RECEPTORS

The present invention relates to a class of substituted tetrahydropyridine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D_\alpha}$ (or 5-HT$_{1D-1}$) and 5-HT$_{1D_\beta}$ (or 5-HT$_{1D-2}$), and their amino acid sequences are disclosed and claimed in WO-A-91/17174.

The 5-HT$_{1D_\alpha}$ receptor subtype in humans is believed to reside on sensory terminals in the dura mater. Stimulation of the 5-HT$_{1D_\alpha}$ subtype inhibits the release of inflammatory neuropeptides which are thought to contribute to the headache pain of migraine. The human 5-HT$_{1D_\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1d}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D_\alpha}$ and 5-HT$_{1D_\beta}$ receptor subtypes (cf. WO-A-91/17174, Table 1), and since it is the blood vessels with which the 5HT$_{1D_\beta}$ subtype is most closely associated, it is believed that the cardiovascular side-effects observed with sumatriptan can be attributed to stimulation of the 5-HT$_{1D_\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D_\alpha}$ receptor subtype, whilst having a less pronounced action at the 5-HT$_{1D_\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D_\alpha}$ receptor subtype. Moreover, the compounds in accordance with this invention have been found to possess at least a 10-fold selective affinity for the 5-HT$_{1D_\alpha}$0 receptor subtype relative to the 5-HT$_{1D_\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the tetrahydropyridine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the substituted piperazine moiety with a differently substituted tetrahydropyridine moiety.

WO-A-91/18897 describes a class of tryptamine derivatives substituted by various five-membered rings, which are stated to be specific to a particular type of "5-HT$_1$-like" receptor and thus to be effective agents for the treatment of clinical conditions, particularly migraine, requiring this activity. A further class of tryptamine derivatives with alleged anti-migraine activity is disclosed in WO-A-94/02460. However, neither WO-A-91/18897 nor WO-A-94/02460 discloses or suggests the tetrahydropyridine derivatives provided by the present invention.

Moreover, nowhere in the prior art mentioned above is there any disclosure of a subtype-selective 5-HT$_{1D}$ receptor agonist having a 5-HT$_{1D_\alpha}$ receptor binding affinity (IC$_{50}$) below 50 nM and at least a 10-fold selective affinity for the 5-HT$_{1D_\alpha}$ receptor subtype relative to the 5-HT$_{1D_\beta}$ subtype.

The compounds according to the present invention are subtype-selective 5-HT$_{1D}$ receptor agonists having a human 5-HT$_{1D_\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D_\alpha}$ receptor subtype relative to the 5-HT$_{1D_\beta}$ subtype. Moreover, the compounds in accordance with this invention possess interesting properties in terms of their efficacy and/or bioavailability.

The present invention provides a compound of formula I, or a salt or prodrug thereof:

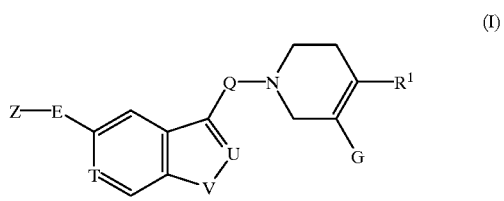

(I)

wherein

Z represents hydrogen, halogen, cyano, nitro, trifluoromethyl, —OR$^5$, —OCOR$^5$, —OCONR$^5$R$^6$, —OCH$_2$CN, —OCH$_2$CONR$^5$R$^6$, —SR$^5$, —SOR$^5$, —SO$_2$R$^5$, —SO$_2$NR$^5$R$^6$, —NR$^5$R$^6$, —NR$^5$COR$^6$, —NR$^5$CO$_2$R$^6$, —NR$^5$SO$_2$R$^6$, —COR$^5$, —CO$_2$R$^5$, —CONR$^5$R$^6$, or a group of formula (Za), (Zb), (Zc) or (Zd):

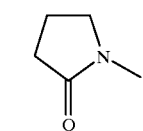
(Za)

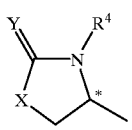
(Zb)

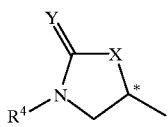
(Zc)

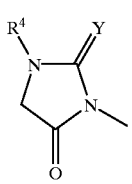
(Zd)

in which the asterisk * denotes a chiral centre: or

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

X represents oxygen, sulphur, —NH— or methylene:

Y represents oxygen or sulphur;

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents nitrogen or CH;

U represents nitrogen or C—$R^2$;

V represents oxygen, sulphur or N—$R^3$;

G represents halogen, trifluoromethyl, $C_{1-6}$ alkyl, $C_{1-6}$ alkoxy, halo($C_{1-6}$)alkyl or $C_{1-6}$ alkoxy($C_{1-6}$)alkyl;

$R^1$ represents $C_{3-6}$ alkenyl, $C_{3-6}$ alkynyl, aryl($C_{1-6}$)alkyl or heteroaryl($C_{1-6}$)alkyl, any of which groups may be optionally substituted;

$R^2$, $R^3$ and $R^4$ independently represent hydrogen or $C_{1-6}$ alkyl; and $R^5$ and $R^6$ independently represent hydrogen, $C_{1-6}$ alkyl, trifluoromethyl, phenyl, methylphenyl, or an optionally substituted aryl($C_{1-6}$)alkyl or heteroaryl($C_{1-6}$)alkyl group; or $R^5$ and $R^6$, when linked through a nitrogen atom, together represent the residue of an optionally substituted azetidine, pyrrolidine, piperidine, morpholine or piperazine ring.

The present invention also provides a compound of formula I as defined above, or a salt or prodrug thereof, wherein G represents halogen, trifluoromethyl, $C_{1-6}$ alkyl, halo($C_{1-66}$)alkyl or $C_{1-6}$alkoxy($C_{1-6}$)alkyl.

Where Z in the compounds of formula I above represents a five-membered heteroaromatic ring, this ring may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$) alkyl, $C_{3-7}$ heterocycloalkyl, heteroaryl, heteroaryl($C_{1-6}$) alkyl, $C_{1-6}$ alkoxy, $C_{1-6}$ alkylthio, amino, $C_{1-6}$ alkylamino, di($C_{1-6}$)alkylamino, halogen, cyano and trifluoromethyl.

The group $R^1$ may be optionally substituted by one or more substituents, as also may the groups $R^5$ or $R^6$ where these represent aryl($C_{1-6}$)alkyl or heteroaryl($C_{1-6}$)alkyl. Where $R^1$, $R^5$ or $R^6$ represents aryl($C_{1-6}$)alkyl or heteroaryl ($C_{1-6}$)alkyl, any optional substitution will suitably be on the aryl or heteroaryl moiety thereof, although substitution on the alkyl moiety thereof is an alternative possibility. Examples of optional substituents thereon include halogen, cyano, trifluoromethyl, triazolyl, tetrazolyl, $C_{1-6}$ alkyltetrazolyl, hydroxy, $C_{1-6}$ alkoxy, $C_{1-6}$ alkylthio, $C_{2-6}$ alkoxycarbonyl, $C_{2-6}$ alkylcarbonyl, $C_{1-6}$ alkylsulphonyl, arylsulphonyl, amino, $C_{1-6}$ alkylamino, di($C_{1-6}$)alkylamino, di($C_{1-6}$)alkylaminomethyl, $C_{2-6}$ alkylcarbonylamino, arylcarbonylamino, $C_{2-6}$ alkoxycarbonylamino, N—($C_{1-6}$) alkyl—N—($C_{2-6}$)alkoxycarbonylamino, $C_{1-6}$ alkylsulphonylamino, arylsulphonylamino, $C_{1-6}$ alkylsulphonylaminomethyl, aminocarbonylamino, $C_{1-6}$ alkylaminocarbonylamino, di($C_{1-6}$) alkylaminocarbonylamino, mono- or diarylaminocarbonylamino, pyrrolidinylcarbonylamino, piperidinylcarbonylamino, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$) alkylaminosulphonyl, aminosulphonylmethyl, $C_{1-6}$ alkylaminosulphonylmethyl and di($C_{1-6}$) alkylaminosulphonylmethyl.

When $R^5$ and $R^6$, when linked through a nitrogen atom, together represent the residue of an azetidine, pyrrolidine, piperidine, morpholine or piperazine ring, this ring may be unsubstituted or substituted by one or more substituents. Examples of suitable substituents include $C_{1-6}$ alkyl, aryl ($C_{1-6}$)alkyl, $C_{1-6}$ alkoxy, $C_{2-6}$ alkoxycarbonyl and $C_{1-6}$ alkylaminocarbonyl. Typical substituents include methyl, benzyl, methoxy, methoxycarbonyl, ethoxycarbonyl and methylaminocarbonyl. In particular, where $R^5$ and $R^6$ together represent the residue of a piperazine ring, this ring is preferably substituted on the distal nitrogen atom by a $C_{2-6}$ alkoxycarbonyl moiety such as methoxycarbonyl or ethoxycarbonyl.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and t-butyl. Derived expressions such as "$C_{1-6}$ alkoxy", "$C_{1-6}$ alkylthio" and "$C_{1-6}$ alkylamino" are to be construed accordingly.

The expression "$C_{2-6}$ alkenyl" as used herein refers to straight-chained and branched alkenyl groups containing from 2 to 6 carbon atoms. Typical examples include vinyl, allyl, dimethylallyl and butenyl groups.

The expression "$C_{2-6}$ alkynyl" as used herein refers to straight-chained and branched alkenyl groups containing from 2 to 6 carbon atoms. Typical examples include ethynyl and propargyl groups.

Typical $C_{3-7}$ cycloalkyl groups include cyclopropyl, cyclobutyl, cyclopentyl and cyclohexyl.

Typical aryl groups include phenyl and naphthyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyrimidinylmethyl, pyrazinylmethyl, quinolylmethyl and isoquinolylmethyl.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. For example, the compounds of formula I above wherein Z represents a group of formula (Zb) or (Zc) have a chiral centre denoted by the asterisk *, which may accordingly be in the (R) or (S) configuration. It is to be understood that all such isomers and mixtures thereof in any proportion are encompassed within the scope of the present invention.

Where E and Q, which may be the same or different, represent straight or branched alkylene chains, these may be, for example, methylene, ethylene, 1-methylethylene, propylene, 2-methylpropylene or butylene. In addition, the alkylene chain Q may be substituted in any position by one or more substituents selected from fluoro and hydroxy giving rise, for example, to a 2-hydroxypropylene, 2-hydroxymethyl-propylene, 2-fluoropropylene or 2-fluoromethyl-propylene chain Q. Moreover, E may represent a chemical bond such that the moiety Z is attached directly to the central fused bicyclic heteroaromatic ring system containing the variables T, U and V.

Suitably, E represents a chemical bond or a methylene linkage.

Representative alkylene chains for Q include propylene, butylene, 2-hydroxypropylene, 2-hydroxymethyl-propylene, 2-fluoropropylene and 2-fluoromethyl-propylene, especially propylene.

The compound of formula I in accordance with the present invention is suitably an indole, benzofuran or benzthiophene derivative of formula IA, an indazole derivative of formula IB, or a pyrrolo[2,3-c]-pyridine derivative of formula IC:

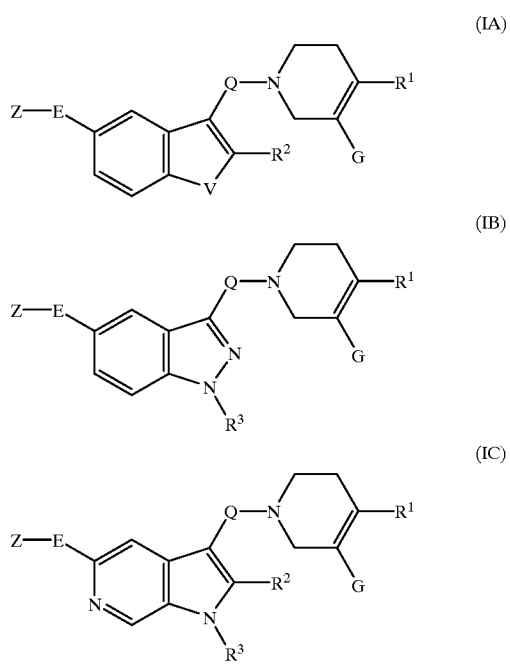

wherein Z, E, Q, V, G, $R^1$, $R^2$ and $R^3$ are as defined above. Preferably, the compounds according to the invention are indole or pyrrolo[2,3-c]pyridine derivatives of formula ID:

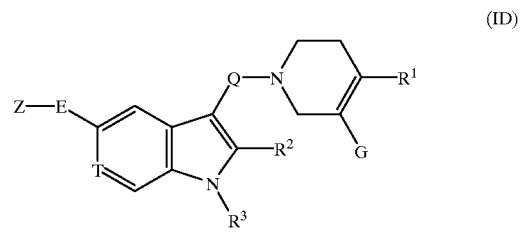

wherein Z, E, Q, T, G, $R^1$, $R^2$ and $R^3$ are as defined above, in particular wherein $R^2$ and $R^3$ are both hydrogen.

Suitable values for the substituent $R^1$ include allyl, dimethylallyl, butenyl, propargyl, benzyl, phenylethyl, phenylpropyl, furylmethyl, thienylmethyl, imidazolylmethyl and pyridylmethyl, any of which groups may be optionally substituted by one or more substituents selected typically from halogen, cyano, trifluoromethyl, triazolyl, tetrazolyl, $C_{1-6}$ alkyl-tetrazolyl, $C_{1-6}$ alkoxy, amino, di($C_{1-6}$)alkylamino di($C_{1-6}$)alkylaminomethyl, $C_{2-6}$ alkylcarbonylamino, $C_{1-6}$ alkoxycarbonylamino, N—($C_{1-6}$) alkyl—N—($C_{2-6}$)alkoxycarbonylamino, $C_{1-6}$ alkylsulphonylamino, aminocarbonylamino, aminocarbonyl, $C_{1-6}$ alkylaminocarbonyl, di($C_{1-6}$) alkylaminocarbonyl, aminosulphonyl, di($C_{1-6}$) alkylaminosulphonyl and $C_{1-6}$ alkylaminosulphonylmethyl.

Particular values of $R^1$ include allyl, dimethylallyl, butenyl, propargyl, benzyl, fluorobenzyl, difluorobenzyl, cyanobenzyl, tetrazolyl-benzyl, methyltetrazolyl-benzyl, methoxybenzyl, aminobenzyl, dimethylaminomethyl-benzyl, acetylamino-benzyl, aminocarbonyl-benzyl, methylaminocarbonyl-benzyl, dimethylaminocarbonyl-benzyl, aminosulphonyl-benzyl, dimethylaminosulphonyl-benzyl, phenylethyl, fluoro-phenylethyl, difluoro-phenylethyl, trifluoromethyl-phenylethyl, cyano-phenylethyl, triazolyl-phenylethyl, amino-phenylethyl, dimethylamino-phenylethyl, acetylamino-phenylethyl, methoxycarbonylamino-phenylethyl, (N-methyl—N—methoxycarbonyl)amino-phenylethyl, aminocarbonylamino-phenylethyl, phenylpropyl, furylmethyl, thienylmethyl, imidazolylmethyl, pyridylmethyl and amino-pyridylmethyl.

Suitably, $R^2$ and $R^3$ independently represent hydrogen or methyl, especially hydrogen.

Suitably, $R^4$ represents hydrogen or methyl, especially hydrogen.

Suitably, $R^5$ and $R^6$ are independently selected from hydrogen, methyl, ethyl, n-propyl, isopropyl, n-butyl, t-butyl, trifluoromethyl, phenyl, methylphenyl (especially 4-methylphenyl), benzyl and phenethyl.

In the compounds of formula I above, the substituent G suitably represents fluoro, trifluoromethyl, methyl, methoxy, fluoroethyl, methoxymethyl or methoxyethyl, alternatively fluoro, trifluoromethyl, methyl, fluoroethyl, methoxymethyl or methoxyethyl, especially methyl, or methoxymethyl.

Suitably, the substituent Z represents hydrogen, fluoro, cyano, hydroxy, methoxy, ethoxy, benzyloxy, methylamino-carbonyloxy, cyano-methoxy, aminocarbonyl-methoxy, methylsulphonyl, aminosulphonyl, N-methylamino-sulphonyl, N,N-dimethylamino-sulphonyl, amino, formylamino, acetylamino, trifluoromethyl-carbonylamino, benzyloxy-carbonylamino, methyl-sulphonylamino, ethyl-sulphonylamino, methylphenyl-sulphonylamino, N-methyl-(N-methylsulphonyl)-amino, N-methyl-(N-ethylsulphonyl)-amino, N-methyl-(N-trifluoromethylsulphonyl)-amino, N-ethyl-(N-methylsulphonyl)-amino, N-benzyl-(N-methylsulphonyl)-amino, N-benzyl-(N-ethylsulphonyl)-amino, acetyl, methoxycarbonyl, ethoxycarbonyl, aminocarbonyl, methylaminocarbonyl, ethylaminocarbonyl, propylaminocarbonyl, butylaminocarbonyl, benzylaminocarbonyl or phenethyl-aminocarbonyl; or a group of formula (Za), (Zb), (Zc) or (Zd) as defined above; or an optionally substituted five-membered heteroaromatic ring as specified above.

In a particular embodiment, Z represents —$SO_2NR^5R^6$ in which $R^5$ and $R^6$ are as defined above. In a subset of this embodiment, $R^5$ and $R^6$ independently represent hydrogen or $C_{1-6}$ alkyl, especially hydrogen or methyl. Particular values of Z in this context include aminosulphonyl, N-methylamino-sulphonyl and N,N-dimethylamino-sulphonyl, especially N-methylamino-sulphonyl.

In another embodiment, Z represents a group of formula (Zb) in which $R^4$ is hydrogen or methyl. In a subset of this embodiment, X and Y both represent oxygen. In a particular aspect of this subset, the chiral centre denoted by the asterisk * is in the (S) configuration.

When the group Z represents an optionally substituted five-membered heteroaromatic ring, this is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4triazole or tetrazole ring. Preferably, the ring is a 1,3-oxazole, 1,3-thiazole, 1,2,4-oxadiazole, 1,2,4thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

A particular sub-class of compounds according to the invention is represented by the compounds of formula IIA, and salts and prodrugs thereof:

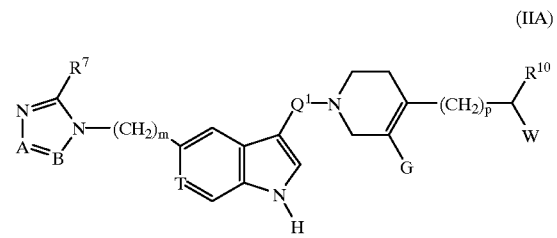

(IIA)

wherein
G is as defined with reference to formula I above;
m is zero, 1, 2 or 3, preferably zero or 1;
p is zero, 1 or 2;
$Q^1$ represents a straight or branched alkylene chain containing from 2 to 5 carbon atoms, optionally substituted in any position by one or more substituents selected from fluoro and hydroxy;
T represents nitrogen or CH;
A represents nitrogen or CH;
B represents nitrogen or C—$R^8$;
$R^7$ and $R^8$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;
W represents a group of formula (Wa), (Wb) or (Wc):

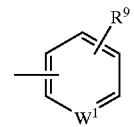

(Wa)

(Wb)

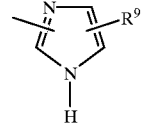

(Wc)

in which
$W^1$ represents CH or nitrogen;
$W^2$ represents oxygen, sulphur, NH or N-methyl;
$R^9$ represents hydrogen, halogen, cyano, trifluoromethyl, triazolyl, tetrazolyl, $C_{1-6}$ alkyl-tetrazolyl, $C_{1-6}$ alkoxy, $C_{2-6}$ alkylcarbonyl, amino, $C_{1-6}$ alkylamino, di($C_{1-6}$)alkylamino, di($C_{1-6}$)alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl, di($C_{1-6}$)alkylaminosulphonyl or $C_{1-6}$ alkylaminosulphonylmethyl; and
$R^{10}$ represents hydrogen or $C_{1-3}$ alkyl.

Suitably, $Q^1$ represents a straight or branched 3 or 4 carbon alkylene chain, optionally substituted in any position by one or more substituents selected from fluoro and hydroxy. Particular alkylene chains for $Q^1$ include propylene, butylene, 2-hydroxypropylene, 2-(hydroxymethyl)-propylene, 2-fluoropropylene and 2-(fluoromethyl)-propylene, especially propylene.

Particular values of $R^7$ and $R^8$ include hydrogen, methyl, ethyl, benzyl and amino, especially hydrogen.

Particular values of $R^9$ include hydrogen, fluoro, cyano, triazolyl, tetrazolyl, methyl-tetrazolyl, methoxy, amino, dimethylaminomethyl, acetylamino, aminocarbonylamino, methylaminocarbonyl, aminosulphonyl and dimethylaminosulphonyl, especially hydrogen or fluoro.

Particular values of $R^{10}$ include hydrogen and methyl.

Another sub-class of compounds according to the invention is represented by the compounds of formula IIB, and salts and prodrugs thereof:

Specific compounds within the scope of the present invention include:
4-benzyl-3-methyl-1-[3-(5-(1,2,4-triazol-4-yl)-1H-indol-3-yl)propyl]-1,2,5,6-tetrahydropyridine;
4-benzyl-3-methoxymethyl-1-[3-(5-(1,2,4-triazol-4-yl)-1H-indol-3-yl)propyl]-1,2,5,6-tetrahydropyridine;
3-methyl-4-(1(RS)-phenylethyl)-1-(3-[5-(1,2,4-triazol-4-yl)-1H-indol-3-yl]propyl)-1,2,5,6-tetrahydropyridine;
4-benzyl-3-methoxy-1-(3-[5-(1,2,4-triazol-4-yl)-1H-indol-3-yl]propyl) -1,2,5,6-tetrahydropyridine;
4-benzyl-3-(2-methoxyethyl)-1-(3-[5-(1,2,4-triazol-4yl)-1H-indol-3-yl]propyl)-1,2,5,6-tetrahydropyridine;
3-methyl-4-(2(RS)-phenylpropyl)-1-(3-[5-(1,2,4-triazol-4-yl)-1H-indol-3-yl]propyl)-1,2,5,6-tetrahydropyridine;
and salts and prodrugs thereof.

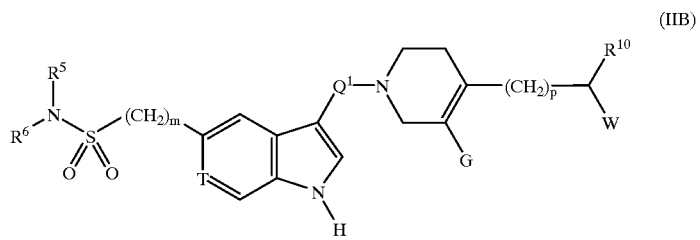

(IIB)

wherein m, p, $Q^1$, T, W and $R^{10}$ are as defined with reference to formula IIA above; and G, $R^5$ and $R^6$ are as defined with reference to formula I above Particular values of $R^5$ and $R^6$ in relation to formula IIB above include hydrogen and $C_{1-6}$ alkyl, especially hydrogen or methyl. Suitably, one of $R^5$ and $R^6$ represents hydrogen and the other represents hydrogen or methyl.

A further sub-class of compounds according to the invention is represented by the compounds of formula IIC, and salts and prodrugs thereof:

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn

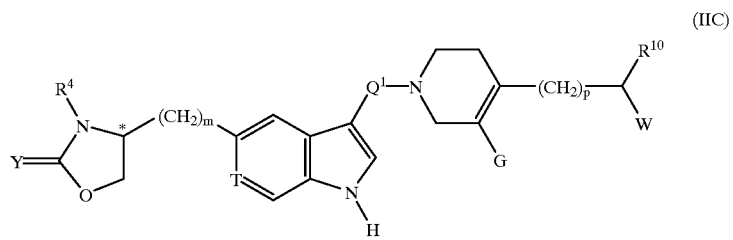

(IIC)

wherein the asterisk * denotes a chiral centre;

m, p, $Q^1$, T, W and $R^{10}$ are as defined with reference to formula IIA above; and G, $R^4$ and Y are as defined with reference to formula I above.

Particular values of $R^4$ in relation to formula IIC include hydrogen and methyl.

Preferably, Y in formula IIC is oxygen.

Preferably, the chiral centre denoted by the asterisk * in formula IIC is in the (S) configuration.

In relation to formulae IIA, IIB and IIC above, the substituent G suitably represents fluoro, trifluoromethyl, methyl, fluoroethyl, methoxymethyl or methoxyethyl, especially methyl or methoxymethyl.

starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein T represents CH, U represents C—$R^2$ and V represents N—$R^3$, corresponding to the indole derivatives of formula ID as defined above wherein T represents CH, may be prepared by a process which comprises reacting a compound of formula III:

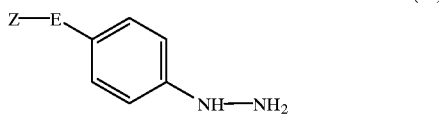

(III)

wherein Z and E are as defined above; with a compound of formula IV, or a carbonyl-protected form thereof:

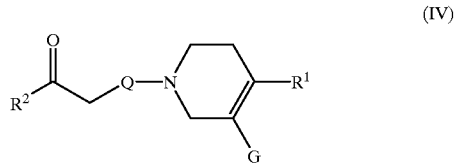

(IV)

wherein Q, G, $R^1$ and $R^2$ are as defined above; followed, where required, by N-alkylation by standard methods to introduce the moiety $R^3$.

The reaction between compounds III and IV, which is an example of the well-known Fischer indole synthesis, is suitably carried out by heating the reagents together under mildly acidic conditions, e.g. 4% sulphuric acid at reflux.

Suitable carbonyl-protected forms of the compounds of formula IV, include the dimethyl acetal or ketal derivatives. Where the alkylene chain Q contains a hydroxy group, this group may condense with the carbonyl moiety in compound IV, whereby the carbonyl moiety is protected in the form of a cyclic hemiacetal.

The Fischer reaction between compounds III and IV may be carried out in a single step, or may proceed via an initial non-cyclising step at a lower temperature to give an intermediate of formula V:

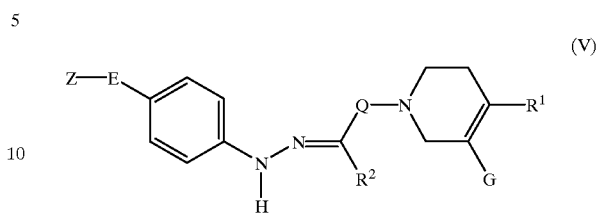

(V)

wherein Z, E, Q, G, $R^1$ and $R^2$ are as defined above; followed by cyclisation using a suitable reagent, e.g. a polyphosphate ester.

The intermediates of formula IV, or carbonyl-protected forms thereof, may be prepared by reacting a compound of formula VI, or a carbonyl-protected form thereof, with a compound of formula VII:

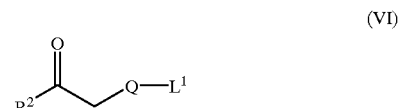

(VI)

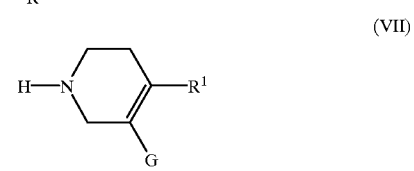

(VII)

wherein Q, G, $R^1$ and $R^2$ are as defined above, and $L^1$ represents a suitable leaving group.

The leaving group $L^1$ is suitably a halogen atom, e.g. chlorine or bromine.

Where $L^1$ represents a halogen atom, the reaction between compounds VI and VII is conveniently effected by stirring the reactants under basic conditions in a suitable solvent, for example potassium carbonate in N,N-dimethylformamide, or triethylamine in tetrahydrofuran or acetonitrile.

In an alternative procedure, the compounds according to the invention may be prepared by a process which comprises reacting a compound of formula VII as defined above with a compound of formula VIII:

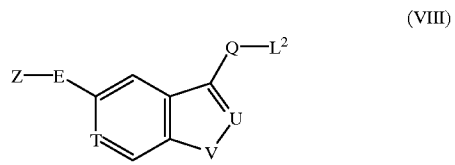

(VIII)

wherein Z, E, Q, T, U and V are as defined above, and $L^2$ represents a suitable leaving group.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compounds VII and VIII is conveniently carried out in a suitable solvent such as 1,2-dimethoxyethane or isopropyl alcohol, typically in the presence of a base such as sodium carbonate or potassium carbonate, optionally with the addition of sodium iodide.

In one representative approach, the compounds of formula VIII wherein T and U both represent CH, V represents NH and $L^2$ represents a mesyloxy or tosyloxy group may be prepared by the sequence of steps illustrated in the following reaction scheme (cf. Larock and Yum, *J. Am. Chem. Soc.,* 1991, 113, 6689):

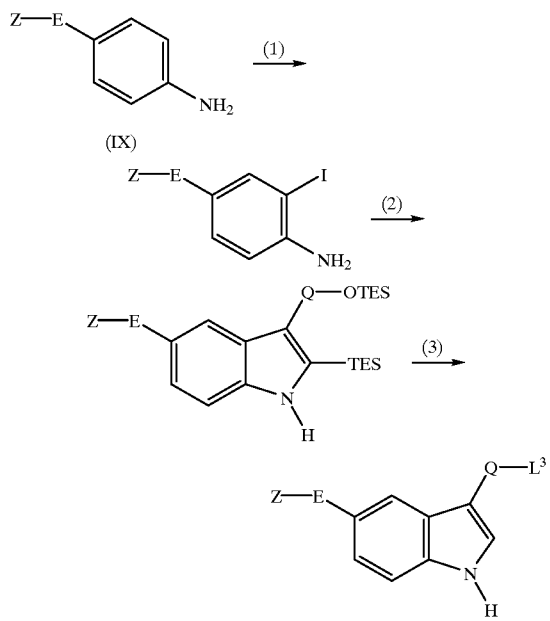

wherein Z, E and Q are as defined above, $L^3$ represents mesyloxy or tosyloxy, and TES is an abbreviation for triethylsilyl.

In Step 1 of the reaction scheme, the aniline derivative IX is treated with iodine monochloride, typically in methanol or acetonitrile, in order to introduce an iodine atom ortho to the amine moiety. Step 2 involves a palladium-mediated coupling reaction with the protected acetylene derivative TES-C≡-C-Q-OTES, typically using palladium acetate and triphenylphosphine in the presence of lithium chloride and sodium carbonate, suitably in N,N-dimethylformamide at an elevated temperature. This is followed in Step 3 by removal of the TES moiety, typically by treatment with hydrochloric acid; followed in turn by mesylation or tosylation, suitably by using mesyl chloride or tosyl chloride respectively in the presence of a base such as triethylamine or pyridine, typically in tetrahydrofuran or dichloromethane/acetonitrile.

In another representative approach, the compounds of formula VIII wherein T and U both represent CH, V represents NH, Q represents a propylene chain and $L^2$ represents a mesyloxy or tosyloxy group may be prepared by reacting 3,4-dihydro-2H-pyran with a compound of formula III as defined above or a salt thereof, under a variant of the Fischer reaction conditions as described above for the reaction between compounds III and IV; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by stirring the pyran derivative with an acid addition salt of the hydrazine derivative III, typically the hydrochloride salt, in an inert solvent such as aqueous ethanol. The resulting hydrazide derivative can then be cyclised by treatment with a Lewis acid such as zinc chloride, in a solvent such as 1,2-dimethoxyethane, suitably at the reflux temperature of the solvent.

In a further procedure, the compounds according to the invention wherein U represents nitrogen and V represents N—$R^3$, corresponding to the indazole derivatives of formula IB as defined above, may be prepared by a process which comprises cyclising a compound of formula X:

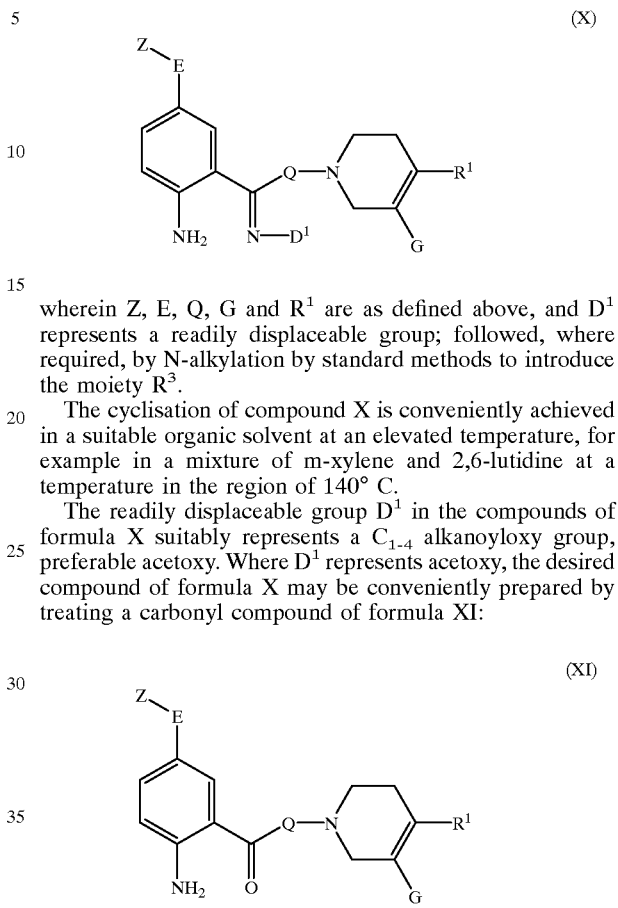

wherein Z, E, Q, G and $R^1$ are as defined above, and $D^1$ represents a readily displaceable group; followed, where required, by N-alkylation by standard methods to introduce the moiety $R^3$.

The cyclisation of compound X is conveniently achieved in a suitable organic solvent at an elevated temperature, for example in a mixture of m-xylene and 2,6-lutidine at a temperature in the region of 140° C.

The readily displaceable group $D^1$ in the compounds of formula X suitably represents a $C_{1-4}$ alkanoyloxy group, preferable acetoxy. Where $D^1$ represents acetoxy, the desired compound of formula X may be conveniently prepared by treating a carbonyl compound of formula XI:

(XI)

[structure]

wherein Z, E, Q, G and $R^1$ are as defined above: or a protected derivative thereof, preferably the N-formyl protected derivative, with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XI may conveniently be prepared by ozonolysis of the corresponding indole derivative of formula XII:

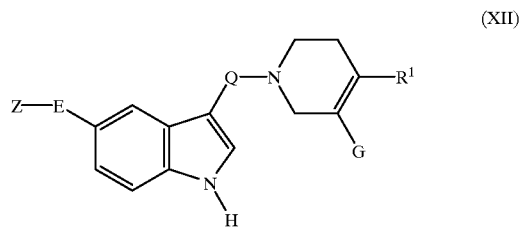

wherein Z, E, Q, G and $R^1$ are as defined above; followed by a reductive work-up, advantageously using dimethylsulphide.

The indole derivatives of formula XII may be prepared by methods analogous to those described in the accompanying Examples or by procedures well known from the art.

In a still further procedure, the compounds according to the invention wherein T represents CH, U represents C—R² and V represents oxygen or sulphur, corresponding to the benzofuran or benzthiophene derivatives of formula IA wherein V is oxygen or sulphur respectively, may be prepared by a process which comprises cyclising a compound of formula XIII:

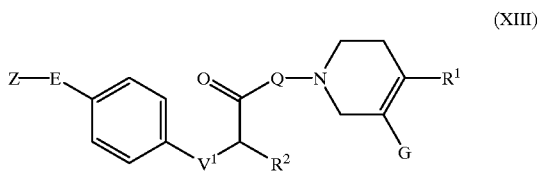

(XIII)

wherein Z, E, Q, G, R¹ and R² are as defined above, and V¹ represents oxygen or sulphur.

The cyclisation of compound XIII is conveniently effected by using polyphosphoric acid or a polyphosphate ester, advantageously at an elevated temperature.

The compounds of formula XIII may be prepared by reacting a compound of formula XIV with a compound of formula XV:

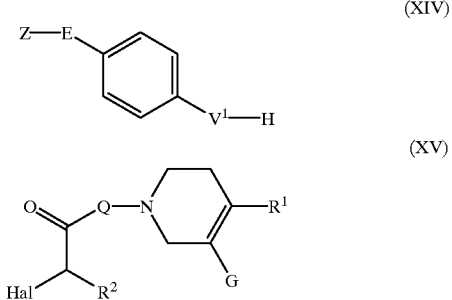

(XIV)

(XV)

wherein Z, E, Q, G, R¹, R² and V¹ are as defined above, and Hal represents a halogen atom.

The reaction is conveniently effected in the presence of a base such as sodium hydroxide.

The hydroxy and mercapto derivatives of formula XIV may be prepared by a variety of methods which will be readily apparent to those skilled in the art. One such method is described in EP-A-0497512.

In a yet further procedure, the compounds according to the invention may be prepared by a process which comprises reducing a compound of formula XVI:

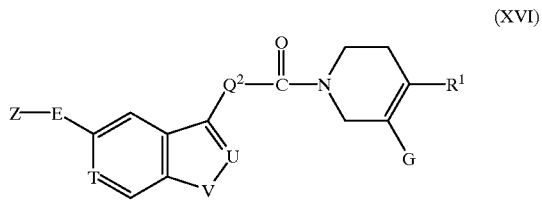

(XVI)

wherein Z, E, T, U, V, G and R¹ are as defined above, and —Q2—CH₂— corresponds to the moiety Q as defined above.

The reduction of compound XVI is conveniently effected by treating the appropriate compound with a reducing agent such as lithium aluminium hydride in an appropriate solvent, e.g. diethyl ether or tetrahydrofuran, or mixtures thereof.

The compounds of formula XVI above may suitably be prepared by reacting the appropriate compound of formula VII as defined above with a compound of formula XVII:

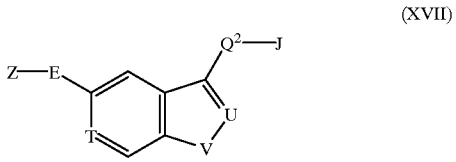

(XVII)

wherein Z, E, T, U, V and Q² are as defined above, and J represents a reactive carboxylate moiety.

Suitable values for the reactive carboxylate moiety J include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XVII above wherein J is an acid chloride moiety may be prepared by treating the corresponding carboxylic acid derivative with thionyl chloride in toluene. Similarly, the intermediates of formula XVII wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula VII.

The hydrazine derivatives of formula III above may be prepared by methods analogous to those described in EP-A-0438230, EP-A-0497512, EP-A-0548813 and WO-A-91/18897, as also may the aniline derivatives of formula IX.

Where they are not commercially available, the starting materials of formula VI, VII, XV and XVII may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I initially obtained wherein the R¹ moiety is substituted by nitro or cyano may be converted by catalytic hydrogenation to the corresponding amino-or aminomethyl-substituted compound respectively. Additionally, a compound of formula I wherein the R¹ moiety is substituted by hydroxy, possibly obtained by lithium aluminium hydride reduction of a precursor alkoxycarbonyl derivative, may be mesylated under standard conditions, and the mesyl group subsequently displaced by an amino moiety by treatment with the desired amine in a sealed tube at an elevated temperature. The amine derivative resulting from any of these procedures may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine; or reductively alkylated by treatment with the appropriate aldehyde or ketone in the presence of sodium cyanoborohydride. If desired, the amine derivative may also be carbamoylated by treatment with the requisite alkyl chloroformate. A compound of formula I initially obtained wherein the R¹ moiety is substituted by cyano may be converted, by treatment with sodium azide, to the corresponding tetrazole derivative, which in turn may be alkylated on the tetrazole ring by treatment with an alkyl halide under standard conditions. By way of additional illustration, a compound of formula I initially obtained wherein the $R^1$ moiety is substituted by an alkoxycarbonyl moiety may be saponified, by treatment with an alkali metal hydroxide, to the corresponding carboxy-substituted compound, which in turn may be converted to an amide derivative by treatment with the appropriate amine, advantageously in the presence of 1-(3-dimethylaminopropyl)-3-ethylcarbodiimide hydrochloride and 1-hydroxybenzotriazole. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in N,N-dimethylformamide.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the $5\text{-HT}_{1D_\alpha}$ receptor subtype, inhibit forskolin-stimulated adenylyl cyclase activity, and stimulate [$^{35}$S]-GTPγS binding to membranes from clonal cell lines expressing human cloned receptors.

$5\text{-HT}_{1D_\alpha}/5\text{-HT}_{1D_\beta}$ Radioligand Binding

Chinese hamster ovary (CHO) clonal cell lines expressing the human $5\text{-HT}_{1D_\alpha}$ and $5\text{-HT}_{1D_\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, CaCl$_2$4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which IC$_{50}$ (the molar concentration of compound necessary to inhibit binding by 50%) values could be calculated for each test compound. The IC$_{50}$ values for binding to the $5\text{-HT}_{1D_\alpha}$ receptor subtype obtained for the compounds of the accompanying Examples were below 50 nM in each case. Furthermore, the compounds of the accompanying Examples were all found to possess a selective affinity for the $5\text{-HT}_{1D_\alpha}$ receptor subtype of at least 10-fold relative to the $5\text{-HT}_{1D_\beta}$ subtype.

$5\text{-HT}_{1D_\alpha}/5\text{-HT}_{1D_\beta}$ Adenylyl Cyclase Assay

Studies were performed essentially as described in *J. Pharmacol. Exp. Ther.*, 1986, 238, 248. CHO clonal cell lines expressing the human cloned $5\text{-HT}_{1D_\alpha}$ and $5\text{-HT}_{1D_\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM MgCl$_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the $5\text{-HT}_{1D_\alpha}$ receptor obtained for the compounds of the accompanying Examples were below 500 nM in each case. Moreover, the compounds of the accompanying Examples which were tested were all found to possess at least a 10-fold selectivity for the $5\text{-HT}_{1D_\alpha}$ receptor subtype relative to the $5\text{-HT}_{1D_\beta}$ subtype.

$5\text{-HT}_{1D_\alpha}/5\text{-HT}_{1D_\beta}$ GTPγS Binding

Studies were performed essentially as described in *Br. J. Pharmacol.*, 1993, 109, 1120. CHO clonal cell lines ex-pressing the human cloned $5\text{-HT}_{1D_\alpha}$ and $5\text{-HT}_{1D_\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, MgCl$_2$10, pargyline 0.01; ascorbate 0.1%: pH 7.4 at room temperature) at a concentration of 40 µg protein/ml for the 5-HT$_{1D_\alpha}$ receptor transfected cells and 40–50 µg protein/ml for the 5-HT$_{1D_\beta}$ receptor transfected cells. The membrane suspension was then incubated, in a volume of 1 ml, with GDP (100 µM for 5-HT$_{1D_\alpha}$ receptor transfected cells, 30 µM for the 5-HT$_{1D_\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D_\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D_\alpha}$ receptor subtype relative to the 5-HT$_{1D_\beta}$ subtype.

EXAMPLE 1

4-Benzyl-3-methyl-1-(3-[5-(1,2,4-triazol-4-yl)-1H-indol-3-yl]propyl)-1,2,5,6-tetrahydropyridine Hydrogen Oxalate a) 4-Benzyl-3-methylpyridine The title compound was obtained from benzyl bromide and 3-methylpyridine as described in *Synthesis*, 1991, 849–850. MS, ES$^+$, m/z=184 for (M+H)$^+$.

b) 4-Benzyl-3-methyl-1,2,5,6-tetrahydropyridine Hydrochloride

The foregoing pyridine (3.8 g, 20.7mmol) in acetone (60 ml) was treated with benzyl bromide (2.8 ml, 23 mmol) then stirred at ambient temperature for 20 hours. The solid was collected, washed with diethyl ether/acetone (1:1), dried to give the quaternary salt (4.90 g, 69%). This salt (2.5 g, 7 mmol) in ethanol (125 ml), at 5° C., was treated portionwise with sodium borohydride (0.3 g, 7.9 mmol) then stirred at 5° C. for 8 hours. The solvent was evaporated then the residue was partitioned between water and dichloromethane. The organic layer was separated and the aqueous re-extracted with dichloromethane (×2). The combined organics were dried (sodium sulphate) then evaporated to afford the 1,2, 5,6-tetrahydropyridine (1.9 g, 98%) as a gum. MS, ES$^+$, m/z=278 for (M+H)$^+$. This crude product (1.9 g, 6.86 mmol) in dichloromethane (100 ml) was cooled to 0° C. then treated with α-chloroethyl chloroformate (0.9 ml, 8.3 mmol), stirred at 0° C. for 1 hour then at ambient temperature for 3 hours. The solvent was evaporated and the residue dissolved in methanol (40 ml) and heated at reflux for 45 minutes. The methanol was evaporated then the residue was dissolved in a minimum volume of hot methanol. On cooling the title product crystallised (0.55 g, 36%), δ$_H$ (250 MHz, CDC$_3$) 1.80 (3H, s), 2.27–2.31 (2H, m), 3.14–3.22 (2H,m), 3.44 (2H, s), 3.58–3.62 (2H, m), 7.10–7.33 (5H, m).

c) 3-(5-[1,2,4-Triazol-4-yl]-1H-indol-3-yl)propan-1-ol

A solution of 4-(1,2,4-triazol-4-yl)phenylhydrazine (25 g, 143 mmol) in dioxan (250 ml) was treated with dihydropyran (24 g, 286 mmol) followed by 1M hydrochloric acid (150 ml) and heated at reflux for 18 hours. The solvent was evaporated, treated with toluene then reevaporated. Inorganic solids were removed by treating the residue with a mixture of methanol and acetonitrile. The mother liquors were purified by column chromatography on silica using dichloromethane/methanol (9:1→4:1) as the eluant. The compound was recrystallised from methanol/acetonitrile to afford the title compound a a colourless solid (10.24 g, 30%), mp 205–207° C. (Found: C, 64.37; H, 5.76; N, 22.83. C$_{13}$H$_{14}$N$_4$O requires C, 64.45; H, 5.82; N, 23.13%). MS, ES$^+$, m/z=243 for (M+H)$^+$; δ$_H$ (360 MHz, DMSO-d$_6$) 1.81 (2H, quintet, J=8 Hz), 2.75 (2H, t, J=8 Hz), 3.46 (2H, dt, J$_1$=5, J$_2$=8 Hz), 4.43 (1H, t, J=5 Hz), 7.26 (1H, d, J=2 Hz), 7.29 (1H, dd, J$_1$=2, J$_2$=9 Hz), 7.47 (1H, d, J=9 Hz), 7.77 (1H, d, J=2 Hz), 9.01 (2H, s), 11.05 (1H, br s).

d) 4-Benzyl-3-methyl-1-(3-[5-(1,2,4-triazol-4-yl)-1H-indol-3-yl]propyl) -1.2,5,6-tetrahydropyridine Hydrogen Oxalate A stirred suspension of 3-(5-[1,2,4-triazol-4-yl]-1H-indol-3-yl)propan-1-ol (0.45 g, 1.86 mmol) in anhydrous tetrahydrofuran (150 ml), under a nitrogen atmosphere, was treated with triethylamine (0.704 ml, 5 mmol) followed by methanesulphonyl chloride (0.35 ml, 4.5 mmol). The reaction mixture was stirred at ambient temperature for 45 minutes. The mixture was filtered then the solvent evaporated. The residue was dissolved in dichloromethane (50 ml) and washed with water (30 ml). The organic layer was dried (sodium sulphate), the solvent was evaporated then the crude mesylate was suspended in propan-2-ol (100 ml), treated with potassium carbonate (0.56 g, 4.1 mmol) and 4-benzyl-3-methyl-1.2.5.6-tetrahydropyridine free base (0.60 g, 3.2 mmol). The reaction mixture was stirred whilst heating at reflux for 18 hours. The solvent was evaporated and the residue partitioned between dichloromethane (50 ml) and water (30 ml). The organic layer was separated and the aqueous re-extracted with dichloromethane (50 ml). The combined organics were dried (sodium sulphate) then the solvent evaporated and the crude product purified by short (plug) column chromatography on silica using 5% methanol in dichloromethane. The title compound free base was obtained (0.40 g, 52%) as a gum. The hydrogen oxalate salt had mp>190° C. (dec.). (Found: C, 66.29: H, 6.41; N, 13.33. C$_{26}$H$_{29}$N$_5$. C$_2$H$_2$O$_4$. 0.45H$_2$O) requires C, 65.98; H, 6.31: N, 13.74%). MS, ES$^+$, m/z=412 for M+H)$^+$; δ$_H$ (360 MHz, DMSO-d$_6$) 1.72 (3H, s), 2.01–2.22 (4H, m), 2.78 (2H, t, J=7 Hz), 3.00–3.24 (4H, m), 3.41 (2H, s), 3.57 (2H, s), 7.12–7.36 (7H, m), 7.50 (1H, d, J=8 Hz), 7.80 (H, d, J=2 Hz), 9.01 (2H, s), 11.19 (1H, s).

EXAMPLE 2

4-Benzyl-3-methoxymethyl-1-(3-[5-(1,2,4-triazol-4-yl)-1H-indol-3-yl]propyl)-1,2,5,6-tetrahydropyridine Hydrogen Oxalate a) 3-Methoxymethylpyridine A solution of 3-hydroxymethylpyridine (10 g, 92 mmol) in anhydrous tetrahydrofuran (200 ml), under an atmosphere of nitrogen, was treated with sodium hydride (4 g of a 55% oil dispersion, 92 mmol) in portions. After stirring for 15 minutes iodomethane (5.7 ml, 92 mmol) was added dropwise and the reaction mixture was stirred at ambient temperature for 2 hours. Water (20 ml) was added and the tetrahydrofuran evaporated. The residue was partitioned between water (50 ml) and dichloromethane (70 ml). The organic layer was separated, dried (sodium sulphate) then evaporated. The crude product was purified by column chromatography on silica using ethyl acetate. The title compound was obtained (11 g, 93%) as an oil, $\delta_H$ (250 MHz, CDCl$_3$) 3.42 (3H, s), 4.48 (2H, s), 7.27–7.32 (1H, m), 7.66–7.71 (1H, m), 8.53–8.60 (2H, m).

b) 4-Benzyl-3-methoxymethylpyridine

The title compound was obtained (4.5 g, 48%) from benzyl bromide and 3-methoxymethylpyridine as described in *Synthesis*, 1991, 849–850. MS, ES$^+$, m/z=214 for (M+H)$^+$; $\delta_H$ (360 MHz, CDCl$_3$) 3.38 (3H, s), 4.11 (2H, s), 4.46 (2H, s), 7.00–7.33 (6H, m), 8.40–8.56 (2H, m).

c) 4-Benzyl-3-methoxymethyl-1,2,5,6-tetrahydropyridine Hydrochloride

The title compound was obtained from 4-benzyl-3-methoxymethylpyridine as described in Example 1. MS, ES$^+$, m/z=218 for (M+H)$^+$; $\delta_H$ (250 MHz, CDCl$_3$) 2.33–2.37 (2H, m), 3.16–3.22 (2H, m), 3.33 (3H, s), 3.49 (2H, s), 3.74–3.78 (2H, m), 4.09 (2H, s), 7.11–7.34 (5H, m).

d) 4-Benzyl-3-methoxymethyl-1-(3-[5-(1,2,4-triazol-4-yl)-1H-indol-3-yl]propyl)-1,2,5,6-tetrahydropyridine Hydrogen Oxalate The title compound free base was obtained (0.16 g, 35%) from the mesylate obtained from 3-(5-[1,2,4-triazol-4-yl]-1H-indol-3-yl)propan-1-ol and 4-benzyl-3-methoxymethyl-1,2,5,6-tetrahydropyridine as described in Example 1. The hydrogen oxalate salt had mp>105° C. (dec.). (Found: C, 61.76; H, 6.04; N, 11.52. C$_{27}$H$_{31}$N$_5$O. 1.7C$_2$H$_2$O$_4$ requires C, 61.41; H, 5.83; N, 11.78%). MS, ES$^+$, m/z=442 for (M+H)$^+$; $\delta_H$ (360 MHz, DMSO-$_6$) 2.02–2.16 (2H, m), 2.18–2.31 (2H,m), 2.78 (2H, t, J=7 Hz), 3.09–3.32 (4H, m), 3.24 (3H, s), 3.49 (2H, s), 3.71 (2H, br s), 4.05 (2H, s), 7.13–7.36 (7H, m), 7.50 (1H, d, J=8 Hz), 7.81 (1H, d, J=2 Hz), 9.01 (2H, s), 11.19 (1H, s).

EXAMPLE 3

3-Methyl-4-(1(RS)-phenylethyl)-1-(3-[5-(1,2,4-triazol-4-yl)-1H-indol-3-yl]propyl)-1,2,5,6-tetrahydropyridine Hydrogen Oxalate The title compound was obtained as described in Example 1, using 3-methylpyridine and 1(RS)-phenylethylbromide. The hydrogen oxalate salt had mp>120° C. MS, ES$^+$, m/z=426 for (M+H)$^+$ of free base (Found: C, 63.69; H, 6.57; N, 12.23. C$_{27}$H$_{31}$N$_5$. 1.6C$_2$H$_2$O$_4$ requires C, 63.68; H, 6.05; N, 12.29%).

EXAMPLE 4

4-Benzyl-3-methoxy-1-(3-[5-(1,2,4-triazol-4-yl)-1H-indol-3-yl]propyl) -1,2,5,6-tetrahydropyridine Hydrogen Oxalate The title compound was obtained as described in Example 1, using benzylbromide and 3-methoxypyridine (EP 488861). The hydrogen oxalate salt had mp>55° C. (dec.). MS, ES$^+$, m/z=428 for (M+H)$^+$ of free base (Found: C, 61.17; H, 5.77; N, 12.01. C$_{26}$H$_{29}$N$_5$O. 1.5C$_2$H$_2$O$_4$. 0.5H$_2$O requires C, 60.94; H, 5.81; N, 12.25%).

EXAMPLE 5

4-Benzyl-3-(2-methoxyethyl)-1-(3-[5-(1,2,4-triazol-4-yl)-1H-indol-3-yl]propyl)-1,2,5,6-tetrahydropyridine Hydrogen Oxalate a) 4-Benzyl-3-(2-methoxyethyl)-pyridine 4-Benzyl-pyridin-3-yl acetic acid methyl ester (prepared as described in *Synthesis*, 1991, 849–850) (6 g, 23.5 mmol) in anhydrous diethyl ether (150 ml) under nitrogen, was treated dropwise with a solution of lithium aluminium hydride in ether (1M, 26 ml). The reaction mixture was stirred at ambient temperature overnight then treated with 4M sodium hydroxide solution. The mixture was filtered then evaporated. The residue was dissolved in dichloromethane, dried (sodium sulphate), filtered, evaporated then purified by column chromatography on silica using dichloromethane/methanol (gradient) to afford the alcohol as a gum (3.5 g, 70%). This alcohol (1.1 g, 5.2 mmol) in anhydrous tetrahydrofuran (20 ml), under a nitrogen atmosphere, was treated with sodium hydride (230 mg of a 55% oil dispersion, 5.2 mmol). After 15 minutes iodomethane (327 µl, 5.2 mmol) was added and the reaction mixture stirred at ambient temperature overnight. Water was added, then the solvent was evaporated. The residue was partitioned between dichloromethane and water. The organic layer was collected, dried (sodium sulphate), evaporated and the residue purified by column chromatography using dichloromethane/methanol (gradient elution) to afford the title compound as a gum (730 mg, 62%). MS, ES$^+$, m/z=228 for (M+H)$^+$.

b) 4-Benzyl-3-(2-methoxyethyl)-1-(3-[5-(1,2,4-triazol-4-yl)-1H-indol-3-yl]propyl-1,2,5,6-tetrahydropyridine Hydrogen Oxalate The title compound free base was obtained from the foregoing pyridine derivative using the procedure described in Example 1. The hydrogen oxalate salt had mp>84° C. MS, ES$^+$, m/z=456 for (M+H)$^+$. (Found: C, 61.71; H, 6.31; N, 11.70. C$_{28}$H$_{33}$N$_5$O. 1.75C$_2$H$_2$O$_4$ requires C, 61.70; H, 6.00; N, 11.42%).

EXAMPLE 6

3-Methyl-4(2(RS)-phenylpropyl)-1-(3-[5-(1,2,4-triazol-4-yl)-1H-indol-3-yl]propyl)-1,2,5,6-tetrahydropyridine Hydrogen Oxalate a) 3-Methylpyridine-4-carboxaldehyde 1M Lithium aluminium hydride in tetrahydrofuran (6.96 ml, 6.96 mmol) in anhydrous tetrahydrofaran (15 ml) under a nitrogen atmosphere, was cooled to −10° C. and treated with ethyl acetate (0.61 g, 6.96 mmol) dropwise. After 10 minutes this solution was treated with dropwise addition of 3,N-dimethyl-N-phenyl-isonicotinamide (1.50 g, 6.63 mmol, *J. Chem. Res., Synop.* 1986, 20–21) in tetrahydrofuran (15 ml). After 2 hours at −10° C. the mixture was allowed to warm to room temperature. Methanol (10 ml) was added, followed by a saturated solution of potassium tartrate. The organic layer was separated and the aqueous layer was exhaustively extracted with dichloromethane. The combined organics were washed with water (2×10 ml), dried (sodium sulphate) then evaporated. The residue was purified by chromatography on silica using dichloromethane/methanol (40:1) to afford the aldehyde (560 mg, 70%) as a gum. MS, ES$^+$, m/z=122 for (M+H)$^+$, $\delta_H$ (360 MHz, DMSO-d$_6$) 2.59 (3H, s), 7.68 (1H, d, J=5 Hz), 8.66 (1H, s), 8.70 (1H, d, J=5 Hz), 10–30 (1H, s).

b) 1(RS)-(3-Methyl-pyridin-4-yl)-2(RS)-phenyl-propan-1-ol

1-Bromoethylbenzene (2.2 ml, 17 mmol) in anhydrous tetrahydrofuran (30 ml) was added dropwise to a stirred solution of a cooled (−5° C.) mixture of zinc (2.7 g, 41.5 mmol) in anhydrous tetrahydrofuran (5 ml). The mixture was allowed to warm to 5° C. and stirred for 2 hours. This mixture was added to a stirred mixture of copper(1)cyanide (1.25 g, 14 mmol) and lithium chloride (1.25 g, 30 mmol) in tetrahydrofuran (15 ml) at −78° C., under nitrogen. The mixture was allowed to warm to −20° C. for 5 minutes then re-cooled to −78° C. This mixture was treated with boron trifluoride diethyl etherate (3.5 ml, 28 mmol) followed by a solution of the foregoing aldehyde (1.7 g, 14 mmol) in tetrahydrofuran (10 ml). The mixture was allowed to warm to room temperature whilst stirring overnight. The solvent was evaporated and the residue partitioned between water and dichloromethane. The organic layer was dried (sodium sulphate), the solvent evaporated and the residue purified by column chromatography on silica using dichloromethane/methanol (gradient). The title compound was obtained as a mixture of diastereomers (350 mg, 12%). MS, ES$^+$, m/z=228 for (M+H)$^+$.

c) 3-Methyl-4-(2(RS)-phenylpropyl)-pyridine

The foregoing alcohol (340 mg, 1.5 mmol) and zinc (activated, 1 g) in formic acid (5 ml) were heated at reflux for 10 hours. The formic acid was evaporated and the residue treated with saturated potassium carbonate solution then extracted with dichloromethane. The organic layer was dried (sodium sulphate), the solvent evaporated and the residue purified by column chromatography on silica using dichloromethane/methanol (gradient) as eluent. The title compound was obtained (100 mg, 32%) as a gum. MS, ES$^+$, m/z=212 for (M+H)$^+$. $\delta_H$ (250 MHz, CDCl$_3$) 1.31 (3H, d, d) 3-Methyl-4-(2(RS)-phenylpropyl)-1-(3-[5-(1,2,4triazol-4-yl)-1H-indol -3-yl]propyl)-1,2,5,6-tetrahydropyridine Hydrogen Oxalate The title compound was obtained as described in Example 1. using the foregoing pyridine derivative. The hydrogen oxalate salt had mp >49° C. (dec.). MS, ES$^+$, m/z=440 for (M+H)$^+$ of free base.

We claim:

1. A compound of formula I, or a salt thereof:

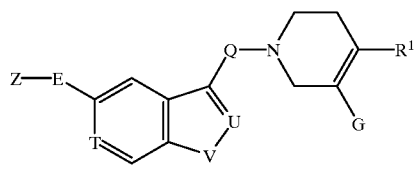

(I)

wherein

Z represents 1,2,4-triazole optionally substituted with C$_{1-6}$ alkyl, C$_{2-6}$ alkenyl, C$_{2-6}$ alkynyl, C$_{3-7}$ cycloalkyl, aryl, aryl(C$_{1-6}$)alkyl, C$_{1-6}$ alkoxy, C$_{1-6}$ alkylthio, amino, C$_{1-6}$ alkylamino, di(C$_{1-6}$)alkylamino, halogen, cyano or trifluoromethyl, wherein aryl represents phenyl or naphthyl;

E represents a chemical bond or a straight or branched alkylene chain containing from 1 to 4 carbon atoms;

Q represents a straight or branched alkylene chain containing from 1 to 6 carbon atoms, optionally substituted in any position by one or more substituents selected from fluoro and hydroxy;

T represents CH;

U represents C—R$^2$;

V represents N—R$^3$;

G represents halogen, trifluoromethyl, C$_{1-6}$ alkyl, C$_{1-6}$ alkoxy, halo(C$_{1-6}$)alkyl or C$_{1-6}$ alkoxy(C$_{1-6}$)alkyl;

R$^1$ represents C$_{3-6}$ alkenyl, C$_{3-6}$ alkynyl, or aryl(C$_{1-6}$) alkyl, wherein aryl is phenyl or naphthyl, any of which groups may be optionally substituted with one or more substituents selected from halogen, cyano, trifluoromethyl, C$_{1-6}$ alkoxy, amino, di(C$_{1-6}$) alkylamino, di(C$_{1-6}$)alkylaminomethyl, C$_{2-6}$ alkylcarbonylamino, C$_{2-6}$ alkoxycarbonylamino, N—(C$_{1-6}$)alkyl-N—(C$_{2-6}$)alkoxycarbonylamino, C$_{1-6}$ alkylsulphonylamino, aminocarbonylamino, aminocarbonyl, C$_{1-6}$ alkylaminocarbonyl, di(C$_{1-6}$) alkylaminocarbonyl, aminosulphonyl, di(C$_{1-6}$) alkylaminosulphonyl, and C$_{1-6}$ alkylaminosulphonylmethyl; and R$^2$ and R$^3$ independently represent hydrogen or C$_{1-6}$ alkyl.

2. 4-Benzyl-3-methyl-1-[3-(5-(1,2,4-triazol-4-yl)-1H-indol-3-yl)propyl]-1,2,5,6-tetrahydropyridine; or 4-benzyl-3-methoxymethyl-1-[3-(5-(1,2,4-triazol-4-yl)-1H-indol-3-yl)propyl]-1,2,5,6-tetrahydropyridine; or a salt thereof.

3. 3-Methyl-4-(1(RS)-phenylethyl)-1-(3-[5-(1,2,4-triazol-4-yl)-1H-indol-3-yl]propyl)-1,2,5,6-tetrahydropyridine; 4-benzyl-3-methoxy-1-(3-[5-(1,2,4-triazol-4-yl)-1H-indol-3-yl]propyl)-1,2,5,6tetrahydropyridine; 4-benzyl-3-(2-methoxyethyl)-1-(3-[5-(1,2,4-triazol-4-yl)-1H-indol-3-yl]propyl)-1,2,5,6-tetrahydropyridine; or 3-methyl-4-(2(RS)-phenylpropyl)-1-(3-[5-(1,2,4-triazol-4-yl)-1H-indol-3-yl]propyl)-1,2,5,6-tetrahydropyridine; or a salt thereof.

4. A pharmaceutical composition comprising a pharmaceutically effective amount of a compound of formula I as defined in claim 1, or a pharmaceutically acceptable salt thereof, and a pharmaceutically acceptable carrier.

5. A method of treating a subject suffering from migraine and associated conditions which comprises administering to that subject a therapeutically effective amount of a compound according to claim 1.

6. A method of treating a subject suffering from migraine and associated conditions as recited in claim 5, wherein said associated conditions are selected from the group consisting of cluster headache, chronic paroxysmal hemicrania, headache associated with vascular disorders, tension headache, and pediatric migraine.

7. A compound according to claim 1 having the formula II A, or a salt thereof:

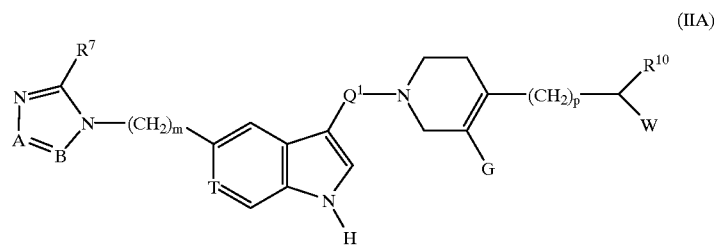

(IIA)

wherein

G and T are as defined with reference to formula I in claim 1;

m is zero, 1, 2 or 3;

p is zero, 1 or 2;

$Q^1$ represents a straight or branched alkylene chain containing from 2 to 5 carbon atoms, optionally substituted in any position by one or more substituents selected from fluoro and hydroxy;

A represents nitrogen and B represents $CR^8$, or alternatively,

B represents nitrogen and A represents CH;

$R^7$ and $R^8$ independently represent hydrogen, $C_{1-6}$alkyl, $C_{2-6}$ alkenyl, $C_{3-7}$cycloalkyl, aryl, aryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;

W represents a phenyl group optionally substituted with one substituent selected from halogen, cyano, trifluoromethyl, $C_{1-6}$ alkoxy, $C_{2-6}$ alkylcarbonyl, amino, $C_{1-6}$ alkylamino, di($C_{1-6}$alkylamino), di($C_{1-6}$) alkylaminomethyl, $C_{2-6}$ alkylcarbonylamino, $C_{1-6}$ alkylsulphonylamino, aminocarbonylamino, $C_{1-6}$ alkylaminocarbonyl, aminosulphonyl, di($C_{1-6}$) alkylaminosulfonyl and $C_{1-6}$ alkylaminosulphonylmethyl; and $R^{10}$ represents hydrogen or $C_{1-3}$ alkyl.

8. A compound as recited in claim 7, wherein $Q^1$ represents a straight or branched 3 or 4 carbon alkylene chain, optionally substituted in any position by one or more substituents selected from fluoro and hydroxy;

$R^7$ and $R^8$ each independently represent hydrogen, methyl, ethyl, benzyl or amino;

W is a phenyl group that is optionally substituted with one substituent selected from fluoro, cyano, methoxy, amino, dimethylaminomethyl, acetylamino, aminocarbonylamino, methylaminocarbonyl, aminosulphonyl and dimethylaminosulphonyl; and $R^{10}$ is hydrogen or methyl.

* * * * *